United States Patent [19]

Hofmann et al.

[11] Patent Number: 5,538,672
[45] Date of Patent: Jul. 23, 1996

[54] FREE-FLOWING WATER-CONTAINING ALKYL SULFATE PASTES

[75] Inventors: Rainer Hofmann, Duesseldorf; Bert Gruber, Bedburg; Andreas Syldath, Duesseldorf; Ditmar Kischkel, Monheim, all of Germany

[73] Assignee: Henkel Kommanditgesellschaft auf Aktien, Duesseldorf, Germany

[21] Appl. No.: 453,134

[22] Filed: May 24, 1995

Related U.S. Application Data

[63] Continuation of Ser. No. 190,136, filed as PCT/EP92/01704, Jul. 7, 1992, abandoned.

[30] Foreign Application Priority Data

Aug. 3, 1991 [DE] Germany .......................... 41 25 792.8

[51] Int. Cl.$^6$ .......................... C11D 1/12; C07C 305/00
[52] U.S. Cl. .......................... 510/537; 558/20; 558/38; 252/353; 510/498; 510/418
[58] Field of Search .......................... 252/89.1, 550, 252/549, 173, 530, 531, DIG. 14; 558/20, 36

[56] References Cited

U.S. PATENT DOCUMENTS

| | | | |
|---|---|---|---|
| 4,675,128 | 6/1987 | Linde et al. | 252/549 |
| 5,158,692 | 10/1992 | Fabry et al. | 252/8.75 |

FOREIGN PATENT DOCUMENTS

| | | |
|---|---|---|
| 0187204 | 7/1975 | Czechoslovakia . |
| 0024711 | 3/1981 | European Pat. Off. . |
| 2371509 | 6/1978 | France . |
| 3447859 | 7/1988 | Germany . |
| 3718896 | 12/1988 | Germany . |
| 0406565 | 3/1934 | United Kingdom . |
| 9102045 | 2/1991 | WIPO . |
| 9207054 | 4/1992 | WIPO . |
| 9216606 | 10/1992 | WIPO . |

*Primary Examiner*—Paul Lieberman
*Assistant Examiner*—Lorna M. Douyon
*Attorney, Agent, or Firm*—Wayne C. Jaeschke; John E. Drach; Henry E. Millson, Jr.

[57] ABSTRACT

Water-containing, free-flowing and pumpable alkyl sulfate pastes having a viscosity, as measured at a shear rate of 10 s$^{-1}$, of 5 Pa.s to 100 Pa.s and preferably 5 Pa.s to 50 Pa.s at temperatures of 50° to 90° C. which contain an alkyl sulfate corresponding to formula I:

$$R^1\text{—O—SO}_3 M^1 \qquad (I)$$

in which $R^1$ is a linear or branched $C_{12\text{-}22}$ alkyl radical and $M^1$ is an alkali metal, ammonium, alkyl ammonium or hydroxyalkyl ammonium ion;

an alkenyl sulfate corresponding to formula II:

$$R^2\text{—O—SO}_3 M^2 \qquad (II)$$

in which $R^2$ is an alkenyl radical containing 16 to 22 carbon atoms and 1, 2 or 3 double bonds and $M^2$ is an alkali metal, ammonium, alkyl ammonium or hydroxyalkyl ammonium ion;

and a process for their preparation.

20 Claims, No Drawings

FREE-FLOWING WATER-CONTAINING ALKYL SULFATE PASTES

This application is a continuation of application Ser. No. 08/190,136, filed as PCT/EP92/01704, Jul. 7, 1992, now abandoned.

BACKGROUND OF THE INVENTION

1. Field of the Invention

This invention relates to free-flowing, pumpable water-containing alkyl sulfate pastes, to a process for the production of alkyl sulfate pastes having improved flow properties by addition of alkenyl sulfates and to the use of such pastes for the production of detergents and cleaning preparations.

2. Statement of Related Art

Anionic surfactants of the alkyl sulfate type, more especially those containing $C_{16-18}$ alkyl radicals, show excellent detergent properties and are used both in liquid and in powder-form detergents and cleaning preparations.

The detergents in question are generally produced from water-containing alkyl sulfate pastes. To avoid unnecessary mass transport, it is an advantage if water-containing surfactant pastes have a high solids content. However, alkyl sulfate pastes can only be concentrated to a certain solids content. In addition, pastes such as these show non-newtonian flow behavior. Above a limit of around 55% by weight solids, the viscosity generally reaches such high values that the pumpability of the surfactant solutions is no longer guaranteed, even at elevated temperatures. Thus, water-containing fatty alcohol sulfate pastes with solids contents of 30 to 70% by weight have such high viscosities and yield points, even at ambient temperature, that they often cannot be transferred from one vessel to another or pump-circulated.

According to EP 024 711, polyalkyl ether glycol sulfates are added to high-viscosity surfactant concentrates to reduce their viscosity. Whereas compounds such as these are eminently suitable for reducing the viscosity of alkyl ether sulfate, alkylaryl ether sulfate, alkyl benzenesulfonate and alkylaryl sulfosuccinate solutions, their performance in the presence of alkyl sulfates, particularly linear primary alkyl sulfates, is often unsatisfactory.

DE-OS 34 47 859 describes the use of alkanesulfonates as viscosity regulators for high-viscosity anionic surfactant concentrates, more especially salts of α-sulfofatty acid esters.

DE-OS 37 18 896 describes the use of alkoxylated alcohols as viscosity regulators for high-viscosity alkyl benzenesulfonate concentrates.

DESCRIPTION OF THE INVENTION

It has now surprisingly been found that water-containing mixtures of unsaturated and saturated alkyl sulfates have a low viscosity and a low yield point so that the unfavorable flow behavior typical of alkyl sulfates based solely on saturated alcohols is overcome. It is thus possible to produce high-solids alkyl sulfate pastes which are flowable and pumpable, even at low temperatures and low shear rates.

Accordingly, the present invention relates to a water-containing, free-flowing and pumpable alkyl sulfate paste having a viscosity, as measured at a shear rate of 10 s$^{-1}$, of 5 Pa.s to 100 Pa.s and preferably 5 Pa.s to 50 Pa.s at temperatures of 50° to 90° C. which contain from 15% by weight to 65% by weight and more particularly from 25% by weight to 50% by weight of an alkyl sulfate corresponding to formula I:

$$R^1-O-SO_3M^1 \qquad (I)$$

in which $R^1$ is a linear or branched $C_{12-22}$ alkyl radical and $M^1$ is an alkali metal, ammonium, alkyl ammonium or hydroxyalkyl ammonium ion, from 5% by weight to 65% by weight and more particularly from 15% by weight to 65% by weight of an alkenyl sulfate corresponding to formula II:

$$R^2-O-SO_3M^2 \qquad (II)$$

in which $R^2$ is an alkenyl radical containing 16 to 22 carbon atoms and 1, 2 or 3 double bonds and $M^2$ is an alkali metal, ammonium, alkyl ammonium or hydroxyalkyl ammonium ion, and from 20% by weight to 50% by weight of water.

The present invention also relates to a process for the production of a free-flowing, pumpable water-containing alkyl sulfate paste having a solids content of 50% by weight to 80% by weight and, more particularly, 60% by weight to 75% by weight, characterized in that an aqueous paste containing 50% by weight to 80% by weight of an alkyl sulfate corresponding to formula I:

$$R^1-O-SO_3-M^1 \qquad (I)$$

in which $R^1$ is a linear or branched $C_{12-22}$ alkyl radical and $M^1$ is an alkali metal, ammonium, alkyl ammonium or hydroxyalkyl ammonium ion, is mixed with an alkenyl sulfate corresponding to formula II:

$$R^2-O-SO_3M^2 \qquad (II)$$

in which $R^2$ is an alkenyl radical containing 16 to 22 carbon atoms and 1, 2 or 3 double bonds and $M^2$ is an alkali metal, ammonium, alkyl ammonium or hydroxyalkyl ammonium ion, in a ratio by weight of alkyl sulfate (I) to alkenyl sulfate (II) of 10:1 to 1:3.

The alkyl sulfate corresponding to formula I and the alkenyl sulfate corresponding to formula II are preferably mixed with one another in a ratio by weight of alkyl sulfate to alkenyl sulfate of 7:1 to 1:2.

In one preferred embodiment of the process according to the invention, a water-containing paste containing an alkenyl sulfate corresponding to formula II is mixed with such a quantity of a water-containing paste containing an alkyl sulfate corresponding to formula I that the sum total of alkyl sulfate and alkenyl sulfate in the resulting water-containing paste is 45% by weight to 80% by weight and more particularly 50% by weight to 75% by weight and the resulting paste contains 20% by weight to 55% by weight and more particularly 25% by weight to 50% by weight of water.

The alkyl sulfates corresponding to formula I are known anionic surfactants which are generally obtained by reaction of aliphatic primary alcohols with a sulfating agent, for example sulfur trioxide or chlorosulfonic acid. Alkyl sulfates to which the process according to the invention extends are preferably derived from $C_{12-22}$ fatty alcohols. Typical examples of such alcohols are lauryl alcohol, myristyl alcohol, cetyl alcohol, stearyl alcohol or behenyl alcohol. A particularly drastic reduction in the viscosity of the paste is observed in the case of alkyl sulfates derived from alcohols containing 12 to 18 carbon atoms and more particularly 16 to 18 carbon atoms.

The alkyl sulfates may also be derived from technical alcohol mixtures such as are formed, for example, in the hydrogenation of technical fatty acid ester mixtures of natural origin or in the hydrogenation of aldehydes from Roelen's oxo synthesis. Alkyl sulfates based on technical coconut oil or hydrogenated palm oil alcohol cuts are preferred. Alcohols such as these are understood to be primary fatty alcohols which have on average the following C chain distribution:

|  | Coconut oil alcohol | Hydrogenated palm oil alcohol |
|---|---|---|
| $C_{10}$: | 0–3% by weight |  |
| $C_{12}$: | 48–58% by weight |  |
| $C_{14}$: | 19–24% by weight | 0–3% by weight |
| $C_{16}$: | 9–12% by weight | 45–55% by weight |
| $C_{18}$: | 11–14% by weight | 45–55% by weight |
| $C_{20}$: |  | 0–3% by weight |

The sulfation products of unsaturated alcohols to be added to the alkyl sulfate pastes in accordance with the invention are compounds which are obtained by reaction of mono-, di- or tri-unsaturated alcohols with sulfating agents, more particularly gaseous sulfur trioxide, and subsequent neutralization and hydrolysis of the reaction products formed. One process for the production of such compounds is described, for example, by M. Morak and K. Audiova in Tenside Detergents 15 (1978), 299.

Since, where unsaturated alcohols are used, the sulfation reaction can also be accompanied by addition of the sulfur trioxide onto the double bond, the alkenyl sulfate paste may also contain substances which contain an internal sulfonate group or a sulfonate group and a sulfate group. The percentage content of these internal sulfonation products is normally from 3 to 20% by weight, based on the quantity of alkenyl sulfate corresponding to formula II. If desired, this quantity may be reduced to zero by corresponding purifying operations.

Typical examples of unsaturated alcohols of which the sulfates corresponding to formula II may be used as the viscosity-reducing component according to the invention are, in particular, palmitoleyl alcohol, oleyl alcohol, elaidyl alcohol, petroselinyl alcohol, linoleyl alcohol, linolenyl alcohol, gadoleyl alcohol or erucyl alcohol. Oleyl alcohol is preferably used. Sulfation products of technical mixtures of the unsaturated alcohols mentioned with one another or with certain quantities of saturated alcohols of corresponding chain length may also be used in the process according to the invention. Pastes such as these preferably contain no more than 70% by weight and, more preferably, from 2% by weight to 60% by weight of saturated alkyl sulfate.

The two starting pastes and also the alkyl sulfate paste according to the invention may contain as further constituents small quantities of generally not more than 10% by weight and more particularly from 2 to 5% by weight, based on the particular paste, of inorganic salts, particularly sulfates, resulting from the reaction of any excess sulfating agent with the neutralization base in the production process.

The highly concentrated alkyl sulfate pastes according to the invention have excellent detergent properties and high solubility in cold water. Accordingly, they are preferably used for the production of powder-form or liquid laundry detergents, dishwashing detergents and cleaning products and also cosmetic products, more particularly hair-care and body-care products.

The products in question may readily be prepared by diluting the pastes produced by the process according to the invention with water to the desired active substance concentration. Other constituents typical of such products may also be added, including in particular builders, such as zeolites and layer silicates, corrosion inhibitors, bleaching agents, bleach activators, optical brighteners, enzymes, redeposition inhibitors, antimicrobial agents, water-miscible solvents, abrasives, foam stabilizers, preservatives, pH regulators, dyes and fragrances and additional surfactants.

EXAMPLES

Example 1

260 g (1 mole) of a technical oleyl/cetyl alcohol (HD-Ocenol® 50-55, a product of Henkel KGaA) with the following composition:

| Myristyl alcohol | 5% by weight |
|---|---|
| Cetyl alcohol | 30% by weight |
| Oleyl alcohol | 65% by weight |
| Iodine value | 53 |
| Hydroxyl value | 215 | were introduced into a 1 liter sulfonation reactor equipped with a jacket cooling system and gas inlet pipe and reacted at 45° C. with 84 g (1.05 mole) of sulfur trioxide. The sulfur trioxide was driven out by heating from a corresponding quantity of 65% by weight oleum, diluted with nitrogen to a concentration of 5% by volume and introduced into the starting product over a period of 30 minutes. The crude sulfonation product was neutralized and, at the same time, hydrolyzed at 80° C. with 214 g of a 20% by weight aqueous sodium hydroxide solution. The reaction product was then adjusted with sodium hydroxide to a pH value of 10. A paste-form product having the following characteristic data was obtained:

| Anionic surfactant content | 59.7% by weight |
|---|---|
| Alkenyl sulfate component | 27.5% by weight |
| Alkyl sulfate component | 20.7% by weight |
| Sulfonate component | 11.5% by weight |
| Unsulfonated components | 2.0% by weight |
| Sodium sulfate | 2.8% by weight |
| Water | 35.5% by weight |

The anionic surfactant content and the unsulfonated components were determined in accordance with DGF-Einheitsmethoden, Stuttgart, 1950–1984, H-III-10 and G-II-6b. The sulfate content was calculated as sodium sulfate, the water content being determined by the Fischer method.

Example 2

Pastes P1 to P3 according to the invention characterized in the following Table were prepared by adding the product according to Example 1 to a 55% by weight water-containing paste of a saturated $C_{16/18}$ alkyl sulfate (Sulfopon® T 55, a product of Henkel KGaA) in the quantities shown in the following Table and mixing. The yield points and viscosities (at a shear rate D of 10 $s^{-1}$) of the pastes thus prepared were measured at 60° C. using a shear-stress-controlled rotational rheometer (Carri-Med® CS 100) with a plate/plate measuring system. The similarly determined values of a solution (C1) free from alkenyl sulfate are shown for comparison.

TABLE

Alkenyl and alkyl sulfate contents [% by weight active substance] and flow data of the pastes

|  | P1 | P2 | P3 | C1 |
|---|---|---|---|---|
| Alkenyl sulfate[a] | 6.88 | 13.75 | 20.62 | — |
| Alkyl sulfate [b] | 46.43 | 37.85 | 29.28 | 55 |
| Yield point [Pa] | 105 | 60 | 25 | 138 |
| Viscosity [Pa · s] | 19 | 12 | 7.5 | 32 |

[a] From corresponding quantities of the product of Example 1
[b] Sum of Na $C_{16/18}$ alkyl sulfate (Sulfopon® T 55, a product of Henkel KGaA) and alkyl sulfate from the product of Example 1

What is claimed is:

1. A water-containing, free-flowing and pumpable alkyl sulfate paste having a viscosity of from about 5 Pa.s to about 100 Pa.s at a shear rate of 10 s$^{-1}$ and at a temperature of from about 50° C. to about 90° C. consisting essentially of from about 15% by weight to about 65% by weight of an alkyl sulfate corresponding to formula I:

$$R^1\text{—O—SO}_3M^1 \quad (I)$$

wherein $R^1$ is a linear or branched $C_{12\text{-}22}$ alkyl radical and $M^1$ is an alkali metal, ammonium, alkyl ammonium or hydroxyalkyl ammonium ion; from about 5% by weight to about 65% by weight of an alkenyl sulfate corresponding to formula II:

$$R^2\text{—O—SO}_3M^2 \quad (II)$$

wherein $R^2$ is an alkenyl radical having from 16 to 22 carbon atoms and 1, 2 or 3 double bonds and $M^2$ is an alkali metal, ammonium, alkyl ammonium or hydroxyalkyl ammonium ion; and from about 20% by weight to about 50% by weight of water wherein the paste contains a solids content of from 60 to 80% by weight.

2. The water-containing alkyl sulfate paste as claimed in claim 1 wherein $R^1$ is a linear or branched $C_{12\text{-}18}$ alkyl radical.

3. The water-containing alkyl sulfate paste as claimed in claim 2 wherein $R^1$ is a linear or branched $C_{16\text{-}18}$ alkyl radical.

4. The water-containing alkyl sulfate paste as claimed in claim 1 wherein $R^2$ is a linear or branched $C_{16\text{-}18}$ alkenyl radical.

5. The water-containing alkyl sulfate paste as claimed in claim 1 wherein said viscosity is from about 5 Pa.s to about 50 Pa.s at a shear rate of 10 s$^{-1}$ and at a temperature of from about 50° C. to about 90° C.

6. A water-containing, free-flowing and pumpable alkyl sulfate paste having a viscosity of from about 5 Pa.s to about 100 Pa.s at a shear rate of 10 s$^{-1}$ and at a temperature of from about 50° C. to about 90° C. consisting essentially of from about 25% by weight to about 50% by weight of an alkyl sulfate corresponding to formula I:

$$R^1\text{—O—SO}_3M^1 \quad (I)$$

wherein $R^1$ is a linear or branched $C_{12\text{-}22}$ alkyl and $M^1$ is an alkali metal, ammonium, alkyl ammonium or hydroxyalkyl ammonium ion; from about 15% by weight to about 65% by weight of an alkenyl sulfate corresponding to formula II:

$$R^2\text{—O—SO}_3M^2 \quad (II)$$

wherein $R^2$ is an alkenyl radical having from 16 to 22 carbon atoms and 1, 2 or 3 double bonds and $M^2$ is an alkali metal, ammonium, alkyl ammonium or hydroxyalkyl ammonium ion; and from about 20% by weight to about 50% by weight of water wherein the paste contains a solids content of from 60 to 80% by weight.

7. The water-containing alkyl sulfate paste of claim 6 wherein the paste contains from about 25% to about 40% by weight of water.

8. The water-containing alkyl sulfate paste as claimed in claim 6 wherein said viscosity is from about 5 Pa.s to about 50 Pa.s at a shear rate of 10 s$^{-1}$ and at a temperature of from about 50° C. to about 90° C.

9. A water-containing, free-flowing and pumpable alkyl sulfate paste having a viscosity of from about 5 Pa.s to about 100 Pa.s at a shear rate of 10 s$^{-1}$ and at a temperature of from about 50° C. to about 90° C. consisting of:

A) from about 15% by weight to about 65% by weight of at least one alkyl sulfate corresponding to formula I:

$$R^1\text{—O—SO}_3M^1 \quad (I)$$

wherein $R^1$ is a linear or branched $C_{12\text{-}22}$ alkyl radical and $M^1$ is an alkali metal, ammonium, alkyl ammonium or hydroxyalkyl ammonium ion;

B) from about 5% by weight to about 65% by weight of at least one alkenyl sulfate corresponding to formula II:

$$R^2\text{—O—SO}_3M^2 \quad (II)$$

wherein $R^2$ is an alkenyl radical having from 16 to 22 carbon atoms and 1, 2 or 3 double bonds and $M^2$ is an alkali metal, ammonium, alkyl ammonium or hydroxyalkyl ammonium ion;

C) small quantities of an internal sulfonation product or products resulting from the preparation of component B);

D) up to 10% by weight of inorganic salts; and

E) from about 20% by weight to about 50% by weight of water; and wherein small quantities of unsulfonated compounds may also be present therein.

10. The water-containing alkyl sulfate paste of claim 9 wherein in component A), $R^1$ is a linear or branched $C_{12\text{-}18}$ alkyl radical.

11. The water-containing alkyl sulfate paste of claim 9 wherein in component B), $R^2$ is a linear or branched $C_{16\text{-}18}$ alkyl radical.

12. The water-containing alkyl sulfate paste of claim 1 wherein said viscosity is from about 5 Pa.s to about 50 Pa.s at a shear rate of 10 s$^{-1}$ and at a temperature of from about 50° C. to about 90° C.

13. The water-containing paste of claim 1 wherein the paste contains from about 25% to about 40% by weight of water.

14. A process for reducing the viscosity of an alkyl sulfate paste comprising the steps of:

I) forming an aqueous paste consisting essentially of from about 50 to about 80% by weight of an alkyl sulfate corresponding to formula I:

$$R^1\text{—O—SO}_3M^1 \quad (I)$$

wherein $R^1$ is a linear or branched $C_{12\text{-}22}$ alkyl radical and $M^1$ is an alkali metal, ammonium, alkyl ammonium or hydroxyalkyl ammonium ion; and II) mixing therewith an aqueous paste consisting essentially of an alkenyl sulfate corresponding to formula II:

$$R^2-O-SO_3M^2 \tag{II}$$

wherein $R^2$ is an alkenyl radical having from 16 to 22 carbon atoms and 1, 2 or 3 double bonds and $M^2$ is an alkali metal, ammonium, alkyl ammonium or hydroxyalkyl ammonium ion; wherein the weight ratio of component I to component II is from about 10:1 to about 1:3, and the resulting paste has a solids content of from about 60 to about 80% by weight.

15. The process of claim 14 wherein said weight ratio is from about 7:1 to about 1:2.

16. The process of claim 14 wherein the amounts of said alkyl sulfate and said alkenyl sulfate mixed together are chosen such that the sum of the weights of said alkyl sulfate and said alkenyl sulfate in the resulting aqueous paste is from about 45% by weight to about 80% by weight and the amount of water is from about 20% by weight to about 55% by weight.

17. The process of claim 16 wherein said sum is from about 50% by weight to about 75% by weight and the amount of water is from about 25% by weight to about 50% by weight.

18. The process of claim 14 wherein the amounts of said alkyl sulfate and said alkenyl sulfate mixed together are chosen such that the sum of the weights of said alkyl sulfate and said alkenyl sulfate in the resulting aqueous paste is from about 50% by weight to about 80% by weight and the amount of water is from about 20% by weight to about 50% by weight.

19. The process of claim 14 wherein the solids content of the water-containing alkyl sulfate paste is from about 60% to about 75% by weight.

20. The product produced by the process of claim 14.

* * * * *